United States Patent [19]

Schönafinger et al.

[11] Patent Number: 4,898,866

[45] Date of Patent: Feb. 6, 1990

[54] THIENYLPIPERAZINONES, THEIR PREPARATION AND THEIR USE

[75] Inventors: Karl Schönafinger, Alzenau; Rudi Beyerle, Frankfurt; Ursula Schindler, Mörfelden-Walldorf, all of Fed. Rep. of Germany

[73] Assignee: Cassella Aktiengesellschaft, Frankfurt, Fed. Rep. of Germany

[21] Appl. No.: 349,540

[22] Filed: May 9, 1989

[30] Foreign Application Priority Data

May 20, 1988 [DE] Fed. Rep. of Germany ....... 3817198

[51] Int. Cl.⁴ .................. A61K 31/495; C07D 403/04
[52] U.S. Cl. ..................................... 514/252; 544/379
[58] Field of Search ......................... 544/379; 514/252

[56] References Cited

U.S. PATENT DOCUMENTS 3,056,784 10/1962 Carr, Jr. et al. ..................... 544/379
3,390,139 6/1968 de Benneville ..................... 544/379
4,598,079 7/1986 Beyerle et al. ..................... 544/379

Primary Examiner—Richard L. Raymond
Assistant Examiner—James H. Turnipseed
Attorney, Agent, or Firm—Perman & Green

[57] ABSTRACT

3-(Thien-2-yl)-piperazin-2-ones, substituted in the 3-position, of the general formula

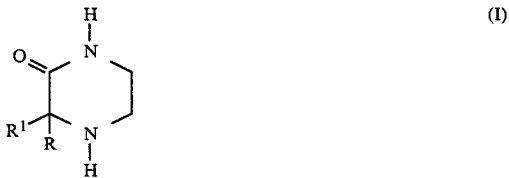

wherein R dentoes, for example, phenyl or $(C_1-C_6)$-alkyl and $R^1$ denotes 2-thienyl and pharmacologically tolerable acid addition salts thereof, which possess valuable nootropic properties. The invention also includes methods for making such compounds, formulations containing such compounds and methods for treating a host in need thereof.

10 Claims, No Drawings

THIENYLPIPERAZINONES, THEIR PREPARATION AND THEIR USE

The invention relates to 3-(thien-2-yl)-piperazin-2-ones, substituted in the 3-position, of the general formula I

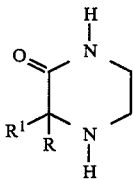

wherein R denotes phenyl; phenyl which is monosubstituted, disubstituted or trisubstituted by $(C_1-C_6)$-alkyl, $(C_1-C_6)$-alkoxy and/or $(C_1-C_6)$-alkoxy-$(C_1-C_6)$-alkyl; $(C_1-C_6)$-alkyl; phenyl-$(C_1-C_6)$-alkyl; naphthyl-$(C_1-C_6)$-alkyl; $(C_1-C_6)$-alkoxy-$(C_1-C_6)$-alkyl; or di-$(C_1-C_6)$-alkylamino-$(C_1-C_6)$-alkyl and $R^1$ denotes 2-thienyl, and to pharmacologically tolerable acid addition compounds thereof.

Including their occurrence as substituents of other radicals, the alkyl and alkoxy radicals can be unbranched or branched and preferably have 1 to 4 C atoms. The substituted phenyl radical represented by R is preferably monosubstituted, particularly in the 2-position or 4-position.

The following are examples of suitable radicals R: methyl; ethyl; isopropyl; propyl; butyl; sec.-butyl; isobutyl; tert.-butyl; pentyl; hexyl; isohexyl; 2-methoxyethyl; 2-ethoxyethyl; 2-propoxyethyl; 2-butoxyethyl, 2-hexyloxyethyl; 3-methoxypropyl; 3-ethoxypropyl; 3-propoxypropyl, 2-methoxypropyl; 2-ethoxypropyl; 2-propoxypropyl; 3- or 4-methoxybutyl, 3- or 4-propoxybutyl, 3- or 4-isopropoxybutyl, 3- or 4-butoxybutyl, 3-, 4- or 5-methoxypentyl, 3-, 4- or 5-ethoxypentyl; 3-, 4- or 5-propoxypentyl; 3-, 4-, 5- or 6-methoxyhexyl; 2-dimethylaminoethyl; 2-diethylaminoethyl; 2-dibutylaminoethyl; 2-dihexylaminoethyl; 2 or 3-dimethylaminopropyl; 2 or 3-diethylaminopropyl; 2 or 3-diaminopropylaminopropyl; 2-, 3- or 4-dimethylaminobutyl; 2-, 3- or 4-diethylaminobutyl; 2-, 3- or 4-dibutylaminobutyl; phenyl; 2-, 3- or 4-methylphenyl, ethylphenyl, propylphenyl, isopropylphenyl, butylphenyl or hexylphenyl; 2-, 3- or 4-methoxyphenyl, ethoxyphenyl, propoxyphenyl, isopropoxyphenyl, butoxyphenyl or pentyloxyphenyl; 2-, 3- or 4-(2-methoxyethyl)-phenyl; 2-, 3- or 4-(2-ethoxyethyl)-phenyl; 2-, 3- or 4-(2-butoxyethyl)-phenyl; 2-, 3- or 4-(3-methoxypropyl)-phenyl; 2-, 3- or 4-(3-ethoxypropyl)-phenyl; 2-, 3- or 4-(3-butoxypropyl)-phenyl; 2,3-, 2,4-, 2,5-, 2,6-, 3,4- or 3,5-dimethylphenyl, 2,3-, 2,4-, 2,5-, 2,6-, 3,4- or 3,5-diethylphenyl, 2,3-, 2,4-, 2,5-, 2,6-, 3,4- or 3,5-dipropylphenyl or 2,3-, 2,4-, 2,5-, 2,6-, 3,4- or 3,5-dibutylphenyl; 2,3-, 2,4-, 2,5-, 2,6-, 3,4- or 3,5-dimethoxyphenyl, 2,3-, 2,4-, 2,5-, 2,6-, 3,4- or 3,5-diethoxyphenyl, 2,3-, 2,4-, 2,5-, 2,6-, 3,4- or 3,5-dipropoxyphenyl, 2,3-, 2,4-, 2,5-, 2,6-, 3,4- or 3,5-diisopropoxyphenyl or 2,3-, 2,4-, 2,5-, 2,6-, 3,4- or 3,5-dibutoxyphenyl; 2,3,4-, 2,3,5-, 2,3,6-, 2,4,5-, 2,4,6-, 2,5,6- or 3,4,5-trimethylphenyl, 2,3,4-, 2,3,5-, 2,3,6-, 2,4,5-, 2,4,6-, 2,5,6- or 3,4,5-triethylphenyl, 2,3,4-, 2,3,5-, 2,3,6-, 2,4,5-, 2,4,6-, 2,5,6- or 3,4,5-tripropylphenyl, 2,3,4-, 2,3,5-, 2,3,6-, 2,4,5-, 2,4,6-, 2,5,6- or 3,4,5-tributylphenyl, 2,3,4-, 2,3,5-, 2,3,6-, 2,4,5-, 2,4,6-, 2,5,6- or 3,4,5-trimethoxyphenyl, 2,3,4-, 2,3,5-, 2,3,6-, 2,4,5-, 2,4,6-, 2,5,6- or 3,4,5-triethoxyphenyl or 2,3,4-, 2,3,5-, 2,3,6-, 2,4,5-, 2,4,6-, 2,5,6- or 3,4,5-tributoxyphenyl; benzyl; 2-phenethyl; 3-phenylpropyl; or 2-(α-naphthyl or β-naphthyl)-ethyl.

Preferred examples of R are methyl, ethyl, isopropyl, phenyl, benzyl and phenethyl; methyl is particularly preferred.

The compounds of the general formula can be prepared by reacting 3-(thien-2-yl)-5,6-dihydro-(1H)-pyrazin-2-one of the formula II

with an organometallic compound of the general formula III

wherein M denotes Li, $(CuLi)_{0.5}$, $Cd_{0.5}$, ZnHal or MgHal (Hal=I, Br or Cl) and R has the meaning already indicated.

The organometallic compounds of the formula III can be prepared in a manner known per se. Grignard compounds RMgHal, organozinc compounds RZnHal and organolithium compounds RLi are prepared in a manner known per se by reacting halogen compounds of the general formula IV

with Mg, Zn or Li in an anhydrous organic solvent, for example an ether or an aliphatic hydrocarbon. In some cases they are also commercially available, such as, for example, methyllithium and n-, sec- and tert-butyllithium. Organocadmium compounds $R_2Cd$ can be obtained from Grignard compounds RMgBr by transmetallization with cadmium bromide $CdBr_2$. Copper-lithium compounds $R_2CuLi$ can be prepared from lithium compounds RLi in ether in accordance with the following equation:

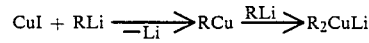

I or Br is preferred for Hal. Of the organometallic compounds III, the Grignard compounds RMgHal are preferred because of their ready accessibility and ease of handling.

The reaction between the compound of the formula II and the compound of the general formula III is normally carried out in an inert organic solvent or dispersing agent. Examples of suitable inert solvents are ethers, in particular ethers having 2 to 8 C atoms in the molecule, such as, for example, diethyl ether, methyl ethyl ether, di-n-propyl ether, diisopropyl ether, methyl n-butyl ether, ethyl propyl ether, dibutyl ether or tetrahydrofuran; 1,4-dioxane, 1,2-dimethoxyethane or bis-β-methoxyethyl ether; oligoethylene glycol dimethyl ethers, such as, for example, pentaglyme; aliphatic hydrocarbons, such as, for example, pentane, hexane, heptane, octane or low-boiling and high-boiling petroleum ethers; and aromatic hydrocarbons, such as, for example, toluene or o-, m- and p-xylene. Mixtures of different inert solvents can also be used.

As is customary in the case of reactions with Grignard reagents or other organometallic compounds, the reaction is advantageously carried out with the exclusion of moisture and, particularly in the case of reactions lasting a fairly long time, under an inert gas. Examples of suitable inert gases are noble gases, such as argon, and nitrogen.

The reaction temperature can vary within wide ranges. In general, the reaction is carried out within the temperature range from 0° C. up to the boiling point of the solvent or solvent mixture used. In many cases the reaction is carried out at temperatures from 0° to 50° C., preferably 15° to 40° C.

The reaction is normally carried out under normal pressure, but can also be carried out under a pressure other than normal pressure.

The reaction mixtures are normally worked up by first hydrolyzing them by adding water and then isolating the desired compound in a customary manner.

The compounds of the formula I can be converted into acid addition salts. Inorganic and organic acids are suitable for the formation of acid addition salts of this type. Examples of suitable acids are hydrogen chloride, hydrogen bromide, naphthalenedisulphonic acid, in particular 1,5-naphthalenedisulphonic acid, phosphoric acid, nitric acid, sulphuric acid, oxalic acid, lactic acid, tartaric acid, acetic acid, salicylic acid, benzoic acid, formic acid, propionic acid, pivalic acid, diethylacetic acid, malonic acid, succinic acid, pimelic acid, fumaric acid, maleic acid, malic acid, sulphamic acid, phenylpropionic acid, gluconic acid, ascorbic acid, isonicotinic acid, methanesulphonic acid, p-toluenesulphonic acid, citric acid or adipic acid. Pharmacologically acceptable acid addition salts are preferred. The acid addition salts can be prepared in the customary manner by combining the compound I and the acid, advantageously in a suitable solvent or diluent. Examples of suitable solvents or diluents are organic solvents, such as alcohols, in particular alcohols having 1 to 6 C atoms, such as, for example, methanol, ethanol or isopropanol, or the ethers already mentioned, and also esters, ketones etc.

3-(Thien-2-yl)-5,6-dihydro-(1H)-pyrazin-2-one of the formula II, which is required as the starting material, is known from Example 42 of U.S. Pat. No. 3,056,784.

The starting compounds of the formulae IV which are required for the preparation of compounds of the formula III are known or can readily be prepared by the processes known for the particular class of compounds.

The piperazinones according to the invention of the formula I and their pharmacologically tolerable salts are nootropic agents, that is to say they are used for the treatment of human diseases which are characterized by a limitation of the brain function, particularly the memory capacity, and for reducing the consequences of cerebral aging processes.

They are superior in effectiveness to known compounds having a similar direction of action. Compared with the compound of Example 16 of EP-A2 72,932 (cf. U.S. Pat. No. 4,598,079), they exhibit a different profile of action while at the same time having an excellent effectiveness.

The compounds according to the invention of the formula I and/or their pharmacologically tolerable acid addition compounds can be administered to humans as medicaments on their own, in mixtures with one another or in the form of pharmaceutical formulations which permit enteral or parenteral application and which contain, as the active constituent, an effective dose of a compound according to the invention and/or one of its salts together with customary, pharmaceutically unobjectionable excipients and additives. The formulations normally contain about 0.5 to 90% by weight of the active compounds according to the invention.

The medicaments can be administered orally, for example in the form of pills, tablets, lacquered tablets, coated tablets, granules, hard and soft gelatine capsules, solutions, syrups, emulsions or suspensions or aerosol mixtures. Administration can, however, also be effected rectally, for example in the form of suppositories, or parenterally, for example in the form of injection solutions, or percutaneously, for example in the form of ointments or tinctures.

The pharmaceutical formulations are prepared in a manner known per se, using pharmaceutically inert inorganic or organic excipients. For the preparation of pills, tablets, coated tablets and hard gelatine capsules it is possible to use, for example, lactose, various grades of starch or derivatives thereof, such as starch hydrolysates, calcium phosphate, cellulose and cellulose derivatives, lactose, hexitols, silicon dioxide, talc, stearic acid or salts thereof etc. Examples of excipients for soft gelatine capsules and suppositories are fats, waxes, synthetic polymers, semi-solid and liquid polyols, natural or hardened oils etc. Examples of excipients suitable for the preparation of solutions and syrups are water, sucrose, invert sugar, glucose, polyols etc. Examples of excipients suitable for the preparation of injection solutions are water, alcohols, glycerol, polyols, vegetable oils etc.

In addition to the active compounds and excipients, the pharmaceutical formulations can also contain additives, such as, for example, fillers, extenders, disintegrants, binders, lubricants, wetting agents, stabilizing agents, emulsifiers, preservatives, sweeteners, colorants, flavouring or aromatizing agents, thickeners, diluents, buffer substances, microbiologically active compounds, such as, for example, preservatives or antiseptics, and also solvents or solubilizers or agents for achieving a depot effect, and also salts for modifying the osmotic pressure, coating agents or antioxidants, in the customary concentrations.

As well as one or more compounds of the general formula I, the pharmaceutical formulations can also contain one or more other pharmaceutically active substances, for example agents which stimulate the blood flow, such as dihydroergocristin, nicergolin, buphenin, nicotinic acid and esters thereof, pyridylcarbinol, bencyclan, cinnarizin, naftidrofuryl, raubasin and vincamin; positively inotropic compounds, such as digoxin, acetyldigoxin, metildigoxin and lanato-glycosides; coronary dilators, such as carbocromen, dipyridamol, nifedipine and perhexilin; anti-angina compounds, such as isosorbide dinitrate, isosorbide mononitrate, glycerol trinitrate, molsidomin and verapamil; β-blockers, such as propranolol, oxprenolol, atenolol, metoprolol and penbutolol, and oogenic-metabolic agents, such as pirilinol. In addition, the compounds can also be combined with other nootropically active substances, such as, for example, piracetam and/or compounds of EP-A2 72,932.

The suitable doses of the active compounds can be varied within wide ranges and thus adjusted to suit the individual requirements of a particular case. As a rule, the daily dose is 0.1 to 150 mg, preferably 1 to 30 mg, per patient for oral application. In the case of other types of application too, thanks to the good absorbability of the active compound, the daily doses are within the same range of quantities.

Nevertheless, it can, in certain cases, be necessary to deviate from the amounts mentioned, specifically as a function of the body weight or the nature of the application, but also on the basis of the point in time or the interval of time at which administratiion is carried out. Thus it can in certain cases be adequate to administer a dose less than the abovementioned amounts.

The daily dose can be administered all at once, but as a rule is administered in several partial doses, for example 2 to 4. The individual dose of the active substance is then 0.001 to 2 mg per kg of body weight, as a rule. Pharmaceutical formulations normally contain 0.1 to 50 mg, preferably 0.1 to 10 mg, of active compound of the formula I or of a pharmacologically acceptable salt per dose.

To demonstrate the pharmacological efficacy of the compounds of the invention the sodium nitrite hypoxia in mice was examined.

In this test using the Gibson and Blass method (J. Neurochem. 27, 37 (1976)) a cerebral hypoxia was induced in mice by administering sodium nitrite (175 mg/kg s.c.) which results in severe behavior disorders in the animals. It is the objective of the test to determine whether pretreatment with the test substances influences the holding capacity on a rotatory rod. The compounds of the invention are administered in dosages of 3 and 30 mg/kg per os, respectively. The results are apparent from the Table below.

Table

Percentage reversal of the disturbance of holding capacity after administration of sodium nitrite and pretreatment with the test substances of formula I

| Compound No. | Substituent R | Dose | Reversal in percent |
|---|---|---|---|
| 1 | phenyl | 30 mg/kg | 73 |
| 2 | methyl | 30 mg/kg | 99 |
| 3 | ethyl | 30 mg/kg | 55 |
| 4 | (3,3-dimethylbutyl) | 3 mg/kg | 51 |
| 5 | H | 30 mg/kg | 24 |

The above compounds 1 to 4 are compounds of the invention and the No. 5 compound is the compound of Example 16 of EP-A2-72932.

The following illustrative embodiments 1 and 2 illustrate the preparation of the compounds according to the invention. Examples A to E relate to pharmaceutical formulations.

EXAMPLE 1

3-Methyl-3-(thien-2-yl)-piperazin-2-one

The Grignard solution prepared from 7.3 g of Mg and 42.6 g of methyl iodide in 150 ml of diethyl ether is added dropwise slowly at room temperature to a solution of 18 g of 3-(thien-2-yl)-5,6-dihydropyrazin-2-one in 150 ml of tetrahydrofuran. Stirring is continued for 15 hours at room temperature and the mixture is then hydrolyzed with 100 ml of water. The pH of the mixture is adjusted to 2 with concentrated HCl, the organic phase is separated off and the aqueous phase is extracted twice by shaking with diethyl ether and its pH is adjusted to 8 with potassium carbonate. The compound is then extracted with methylene chloride. The methylene chloride phase is dried and concentrated. The residual oil is purified by column chromatography over silica gel made by Merck, Darmstadt, type "0.04–0.06", the mobile phase being methylene chloride/methanol in a ratio by volume of 95:5. The fractions containing the compound are concentrated on a rotary evaporator and the residue is recrystallized from isopropanol.

Yield: 8.0 g; melting point 113°–116° C.

EXAMPLE 2

3-Phenyl-3-(thien-2-yl)-piperazin-2-one

The compound is obtained analogously to Example 1 from bromobenzene, magnesium and 3-(thien-2-yl)-4,5-dihydro-pyrazin-2-one.

Yield: 17 g; melting point 159°–161° C. (from isopropanol).

The hydrochloride of this compound is obtained by dissolving the latter in ethanol and adding ethyl acetate saturated with HCl.

Melting point 215°–218° C.

EXAMPLE 3

3-Isopropyl-3-(thien-2-yl)-piperazin-2-one

The compound is obtained analogously to Example 1 from isopropyl chloride, magnesium and 3-(thien-2-yl)-4,5-dihydropyrazin-2-one.

The preparation of the Grignard reagent and the actual reaction were carried out in 1,4-dioxane as solvent.

Melting point 106°–107° C.

EXAMPLE 4

3-(3,3-Dimethylbutyl)-3-(thien-2-yl)-piperazin-2-one

The compound is obtained analogously to Example 1 from 3,3-dimethylbutyl chloride, magnesium and 3-(thien-2-yl)-4,5-dihydro-pyrazin-2-one.

The preparation of the Grignard reagent and the actual reaction were carried out in 1,2-dimethoxyethane as solvent.

Melting point 88°–90° C.

EXAMPLE 5

3-Ethyl-3-(thien-2-yl)-piperazin-2-one

The compound is obtained analogously to Example 1 from ethyl bromide, magnesium and 3-(thien-2-yl)-4,5-dihydro-pyrazin-2-one.

The preparation of the Grignard reagent and the actual reaction were carried out in diethyl ether as solvent.

Melting point 68°–70° C.

EXAMPLE 6

3-(2-Methoxyethyl)-3-(thien-2-yl)-piperazin-2-one

The compound is obtained analogously to Example 1 from 2-methoxyethyl chloride, magnesium and 3-(thien-2-yl)-4,5-dihydropyrazin-2-one.

The preparation of the Grignard reagent and the actual reaction were carried out in bis-$\beta$-methoxyethyl ether as solvent.

Melting point 83°–85° C.

EXAMPLE 7

3-(2-Dimethylaminoethyl)-3-(thien-2-yl)-piperazin-2-one

The compound is obtained analogously to Example 1 from 2j-dimethylaminoethyl chloride, magnesium and 3-(thien-2-yl)-4,5-dihydro-pyrazin-2-one.

The preparation of the Grignard reagent and the actual reaction were carried out in tetrahydrofuran as solvent.

Melting point 77°–80° C.

EXAMPLE A

Soft gelatine capsules containing 5 mg of active compound per capsule:

|  | per capsule |
| --- | --- |
| Active compound | 5 mg |
| Triglyceride mixture fractionated from coconut oil | 150 mg |
| Contents of capsule | 155 mg |

EXAMPLE B

Injection solution containing 1 mg of active compound per ml:

|  | per ml |
| --- | --- |
| Active compound | 1.0 mg |
| Polyethylene glycol 400 | 0.3 ml |
| Sodium chloride | 2.7 mg |
| Water for injection purposes ad | 1 ml |

EXAMPLE C

Emulsion containing 3 mg of active compound per 5 ml

|  | per 100 ml of emulsion |
| --- | --- |
| Active compound | 0.06 g |
| Neutral oil | q.s. |
| Sodium carboxymethylcellulose | 0.6 g |
| Polyoxyethylene stearate | q.s. |
| Pure glycerol | 0.2 to 2.0 g |
| Flavouring | q.s. |
| Water (demineralized or distilled) ad | 100 ml |

EXAMPLE D

Rectal medicament containing 4 mg of active compound per suppository

|  | per suppository |
| --- | --- |
| Active compound | 4 mg |
| Suppository base ad | 2 g |

EXAMPLE E

Tablets containing 2 mg of active compound per tablet

|  | per tablet |
| --- | --- |
| Active compound | 20 mg |
| Maize starch (white) | 30 mg |
| Lactose | 60 mg |
| Soluble starch | 3 mg |
| Magnesium stearate | 2 mg |
|  | 115 mg |

EXAMPLE F

Drops (20 mg in 1 ml = 20 drops)

|  |  |  |
| --- | --- | --- |
| Active compound | 2.00 | g |
| Methylbenzoate | 0.07 | g |
| Ethylbenzoate | 0.03 | g |
| Ethanol, 96% strength | 2 | ml |
| Demineralized water ad | 100 | ml |

It is to be understood that the above described embodiments of the invention are illustrative only and that modificatiions throughout may occur to those skilled in the art. Accordingly, this invention is not to be regarded as limited to the embodiments disclosed herein but is to be limited as defined by the appended claims.

What is claimed is:

1. 3-(Thien-2-yl)-piperazin-2-ones, substituted in the 3-position, of the general formula

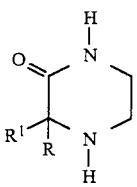

wherein R denotes phenyl; phenyl which is monosubstituted, disubstituted or trisubstituted by $(C_1-C_6)$-alkyl, $(C_1-C_6)$-alkoxy and/or $(C_1-C_6)$-alkoxy-$(C_1-C_6)$-alkyl; $(C_1-C_6)$-alkyl; phenyl-$(C_1-C_6)$-alkyl; naphthyl-$(C_1-C_6)$-alkyl; $(C_1-C_6)$-alkoxy-$(C_1-C_6)$-alkyl; or di-$(C_1-C_6)$-alkylamino-$(C_1-C_6)$-alkyl and $R^1$ denotes 2-thienyl, and pharmacologically tolerable acid addition compounds thereof.

2. Piperazinones according to claim 1, characterized in that R denotes phenyl; phenyl which is monosubstituted, disubstituted or trisubstituted by $(C_1-C_4)$-alkyl, $(C_1-C_4)$-alkoxy and/or $(C_1-C_4)$-alkoxy-$(C_1-C_4)$-alkyl; $(C_1-C_4)$-alkyl; $(C_1-C_4)$-alkoxy-$(C_1-C_6)$-alkyl; phenyl-$(C_1-C_4)$-alkyl; naphthyl-$(C_1-C_4)$-alkyl; or di-$(C_1-C_4)$-alkylamino-$(C_1-C_4)$-alkyl.

3. Piperazinones according to claim 2, characterized in that the phenyl represented by R is monosubstituted.

4. Piperazinones according to claim 1, characterized in that R denotes $(C_1-C_4)$-alkyl.

5. Piperazinones according to claim 1, characterized in that R is selected from the group consisting of methyl, ethyl, isopropyl, phenyl, benzyl and phenethyl.

6. 3-Methyl-3-(thien-2-yl)-piperazin-2-one and pharmacologically tolerable acid addition compounds thereof.

7. 3-Phenyl-3-(thien-2-yl)-piperazin-2-one and pharmacologically tolerable acid addition compounds thereof.

8. Process for the preparation of the piperazin-2-one compounds as defined in claim 1, characterized in that a 3-(thien-2-yl)-5,6-dihydro-(1H)-pyrazin-2-one of the formula II

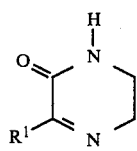

(II)

is reacted with an organometallic compound of the general formula III

R-M  (III)

wherein M is selected from the group consisting of Li, (CuLi)$_{0.5}$, Cd$_{0.5}$, ZnHal or Mg/Hal (Hal=I, Br and Cl) and R has the meaning indicated in claim 1, in an inert organic solvent or solvent mixture within the temperature range from 0° C. up to the boiling point of the solvent or solvent mixture, and the product is worked up in a customary manner and, if appropriate, is converted into a pharmacologically acceptable acid addition compound.

9. Method for improving the human brain function and/or for reducing the consequences of cerebral aging process in humans which comprises administering to a patient in need of such action an effective amount of a compound of claim 1.

10. Pharmaceutical formulation, characterized in that it contains a compound of claim 1 or a pharmacologically acceptable acid addition salt thereof as the active compound, in a pharmacologically effective amount, together with pharmaceutically acceptable excipients and additives and, if appropriate, also one or more other pharmacological active compounds in pharmacologically effective amounts.

* * * * *